(12) United States Patent
Nishiyama et al.

(10) Patent No.: US 6,597,448 B1
(45) Date of Patent: Jul. 22, 2003

(54) APPARATUS AND METHOD OF INSPECTING FOREIGN PARTICLE OR DEFECT ON A SAMPLE

(75) Inventors: Hidetoshi Nishiyama, Fujisawa (JP); Minori Noguchi, Mitsukaido (JP); Yoshimasa Ohshima, Yokohama (JP); Tetsuya Watanabe, Honjyo (JP); Hisato Nakamura, Kodama (JP); Takahiro Jingu, Takasaki (JP); Yuko Inoue, Okegawa (JP); Keiichi Saiki, Hitachinaka (JP); Kenji Watanabe, Oume (JP)

(73) Assignees: Hitachi, Ltd., Tokyo (JP); Hitachi Electronics Engineering Co., Ltd., Tokyo (JP)

( * ) Notice: Subject to any disclaimer, the term of this patent is extended or adjusted under 35 U.S.C. 154(b) by 268 days.

(21) Appl. No.: 09/644,069

(22) Filed: Aug. 23, 2000

(30) Foreign Application Priority Data

Aug. 24, 1999 (JP) ............................................ 11-236510
Mar. 14, 2000 (JP) ............................................ 00-076357

(51) Int. Cl.⁷ .............................................. G01N 21/88
(52) U.S. Cl. ..................... 356/237.4; 356/535; 382/145
(58) Field of Search .......................... 356/237.2–237.5, 356/335, 336, 239.8; 382/145, 191

(56) References Cited

U.S. PATENT DOCUMENTS 6,226,079 B1 * 5/2001 Takeda et al. ........... 356/237.2

* cited by examiner

Primary Examiner—Richard A. Rosenberger
Assistant Examiner—Vincent P. Barth
(74) Attorney, Agent, or Firm—Antonelli, Terry, Stout & Kraus, LLP

(57) ABSTRACT

A system and method of inspecting a foreign particle or a defect on a sample are provided. Such a method comprises irradiating light to an object to be inspected; detecting reflected light or scattered light from the object to be inspected irradiated with the light; detecting a signal of the foreign particle or the defect from the detected signal; providing information related to a size of the foreign particle or the defect from the signal of the detected foreign particle or the defect; and outputting information on a display screen a distribution of the size of the foreign particle or defect with information indicating a cause of the distribution of the foreign particle or defect.

20 Claims, 11 Drawing Sheets

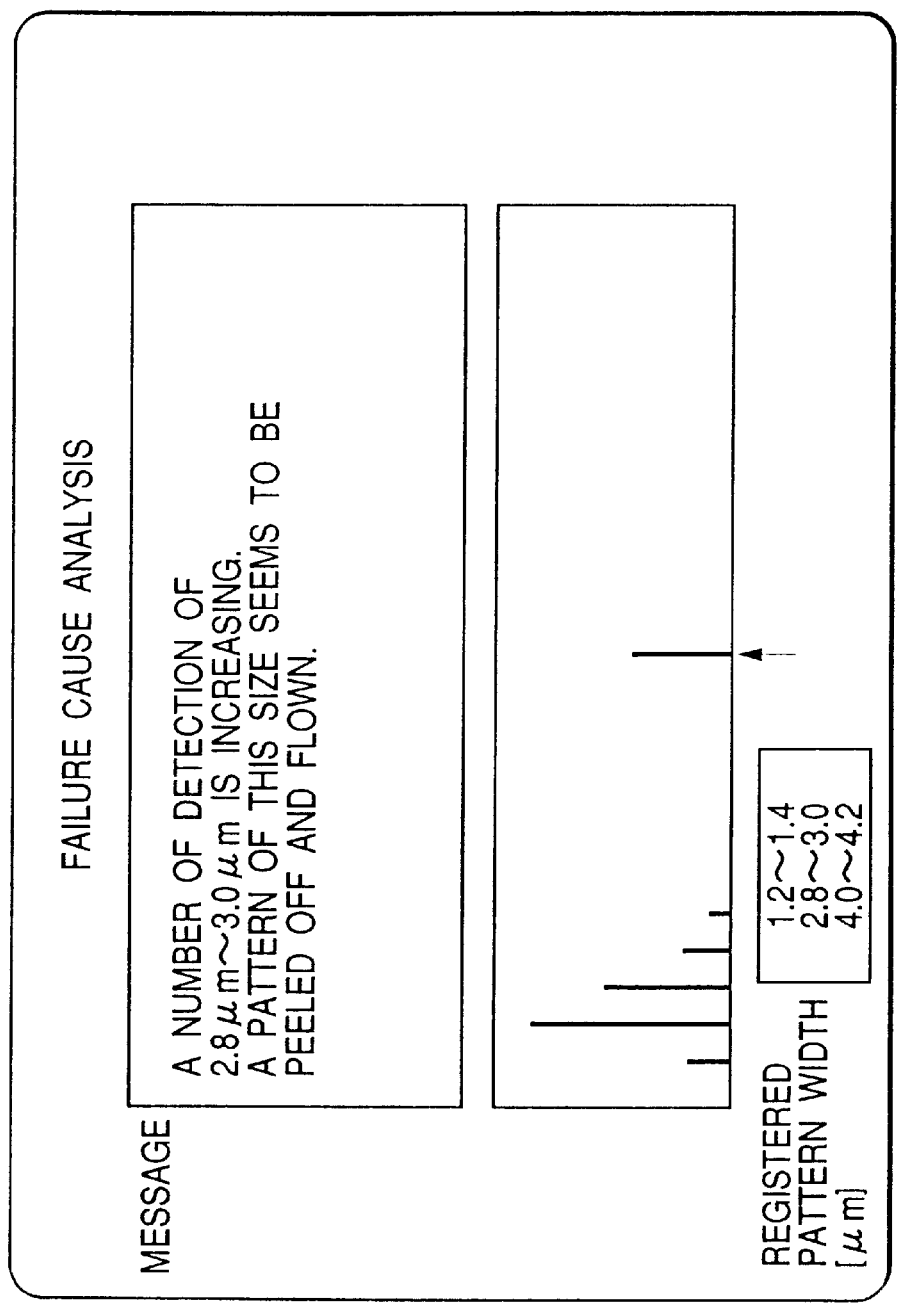

APPARATUS AND METHOD OF INSPECTING FOREIGN PARTICLE OR DEFECT ON A SAMPLE

BACKGROUND OF THE INVENTION

1. Field of the Invention

The present invention relates to an apparatus and a method of inspecting a foreign particle or a defect on a sample. More specifically, the present invention relates to an apparatus and a method of inspecting a foreign particle or a defect on a sample in which a foreign particle present on a substrate and a defect caused on a circuit pattern are detected and displayed so that the cause of failure can be corrected.

2. Prior Art

Conventionally, a technology of detecting a defect on a wafer or the like by optical measuring means has been widely known. For example, according to Japanese Patent Laid-Open No. S62-89336 "Semiconductor wafer inspecting apparatus", there is disclosed a technology of irradiating laser onto a wafer and inspecting a defect by detecting scattered light from a foreign particle generated when the foreign particle is adhered onto the wafer and comparing a result of detection with that of a wafer of the same kind inspected immediately before the detection.

Further, according to Japanese Patent Laid-Open No. H5-273110 "Method and apparatus of measuring size information of particle or defect", there is disclosed a method of measuring a size of a particle or a crystal defect by irradiating an object to be detected with laser beam, receiving scattered light from a particle or a crystal defect of the object to be detected and subjecting the received light to image processing.

Conventionally, in a fabrication line of a wafer, or a substrate for forming a thin film or the like, an inspection system has been used for inspecting a foreign particle or a pattern defect on a substrate and monitoring a transitional change of the number of detection from the foreign particle or defect inspection system and providing a failure analysis on a substrate having a large number of detection with respect of foreign particles or defects on the substrate.

However, according to the conventional technology, a time period required for failure analysis is constituted by "the number of detection multiplied by a failure analysis time period with respect to one foreign particle or defect". In particular, when the number of detection is large in the foreign particle or defect inspection system, an enormous time period is required for failure analysis. As a result, the fabrication of substrates can be delayed significantly.

SUMMARY OF THE INVENTION

It is an object of the present invention to provide a method of inspecting a foreign particle or a defect on a sample and a system thereof capable of carrying out inspection in accordance with a size of a foreign particle or a size of a defect and characteristics of areas of an object to be inspected during a fabrication procedure and providing failure analysis of an object such as a semiconductor wafer or a substrate for forming a thin film.

According to an embodiment of the present invention, a method of inspecting a foreign particle or a defect may be carried out by a procedure of irradiating light to the object to be inspected, a procedure of detecting reflected light or scattered light from the object to be inspected, a procedure of detecting the foreign particle or the defect based on a detected signal, a procedure of carrying out a signal processing based on the detected signal and measuring a size of the foreign particle or the defect, a procedure of processing data for processing a result of inspection and a procedure of displaying information of the result of inspection in this order, the size of the foreign particle or the defect is correlated with failure cause, in the data processing procedure, the failure cause is indicated from a statistical processing of the result of inspection and information of the result of inspection is displayed.

According to the present invention, in carrying out inspection of a fabrication procedure and failure analysis of a semiconductor wafer or a substrate for forming a thin film, there can be provided a method of inspecting a foreign particle or a defect and its system capable of carrying out swift failure countermeasure by carrying out the inspection and the failure analysis in accordance with characteristics of the foreign particle or pattern and characteristics of areas of the object to be inspected.

These and other objects, features and advantages of the invention will be apparent from the following more particular description of preferred embodiments of the invention, as illustrated in the accompanying drawings.

BRIEF DESCRIPTION OF THE DRAWINGS

FIG. 10 is a diagram of a screen displaying cause of failure of causing foreign particles to a user;

DETAILED DESCRIPTION OF THE PREFERRED EMBODIMENTS

An explanation will be given as follows of respective embodiments according to the present invention in reference to FIG. 1 through FIG. 14. (Constitution and operation of inspection system of foreign particle or defect according to the present invention)

First, an explanation will be given of constitution and operation of an inspection apparatus of inspecting a foreign particle or a defect according to an embodiment of the present invention with reference to FIG. 1 and FIG. 2.

In the following, although an explanation will be provided in a case of inspecting a foreign particle on a semiconductor wafer, the present invention is applicable also to an apparatus of inspecting a pattern defect other than a foreign particle. Further, the present invention is applicable not only to a semiconductor wafer but also to a substrate for forming a thin film, a photomask, TFT, PDP and the like.

Figure 1:
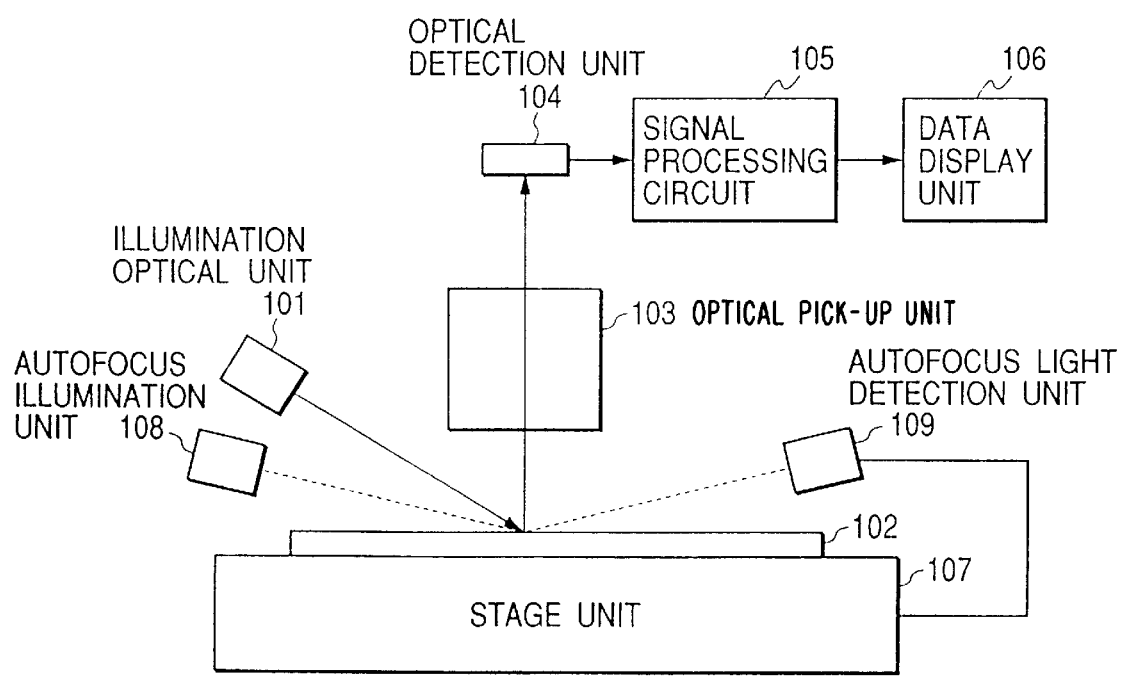
FIG. 1 is a block diagram of an apparatus of inspecting a foreign particle or a defect on a sample according to an embodiment of the present invention.
Figure 2:
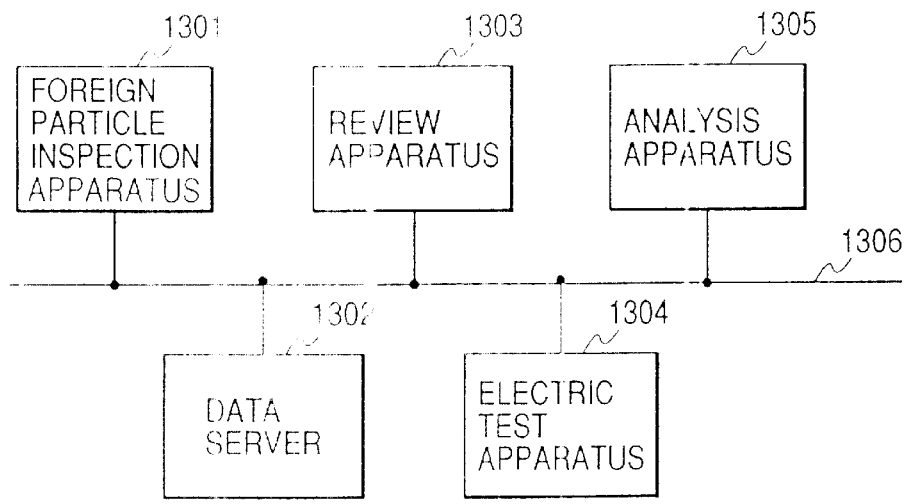
FIG. 2 is a block diagram of an inspection system including an apparatus of inspecting a foreign particle or a defect on a sample according to an embodiment of the present invention.

As shown in FIG. 1, the inspection apparatus comprises an illumination optical unit 101, an optical pick-up unit 103, an optical detection unit 104, a signal processing circuit 105, a data display unit 106, a stage unit 107, an autofocus illumination unit 108 and an autofocus light detection unit 109.

In carrying out inspection, an object to be inspected 102 is mounted on the stage unit 107. Such an object to be inspected 102 is irradiated by the illumination optical unit 101 and scattered light from the object to be inspected 102 is converged by the optical pick-up unit 103. Further, the scattered light from the object to be inspected 102 is detected by the optical detection unit 104. The scattered light detected by the optical detection unit 104 is subjected to photoelectric conversion or the like and subjected to signal processing by the signal processing circuit 105 to thereby detect a foreign object and measure a size thereof.

Further, the object to be inspected 102 is moved in the horizontal direction by the stage unit 107, further, the object to be inspected 102 is moved in the vertical direction to dispose at a focus position of the optical pick-up unit 103 by the autofocus illumination unit 108 and the autofocus light detection unit 109 to thereby enable to detect foreign particles over a total area of the object to be inspected 102 and measure sizes thereof. Further, a result of the detection is displayed on the data display unit 106.

As the illumination optical unit 101, a laser light source of, for example, Ar laser, semiconductor laser or the like may be used to irradiate light onto the object to be inspected 102 by using a beam expander, a collimating lens, a cylindrical lens or the like and is adjusted to irradiate light to a focus position of the optical pick-up unit 103. Further, as the optical pick-up unit 103, an optical lens may be used such that scattered light from the object to be inspected 102 in light irradiated by the illumination optical system 101 is converged to the object to be detected by the optical detection unit 104. Further, the optical pick-up unit 103 may also be configured to carry out an optical processing with regard to the scattered light, for example, change, adjustment or the like of optical properties by a polarizer or a spatial filter.

The optical detection unit 104 is used for detecting the scattered light converged by the optical pick-up unit 103 and subjecting the scattered light to photoelectric conversion, such as, for example, a TV camera, a CCD linear sensor, a TDI sensor, and an antiblooming TDI sensor or a photomultiplier. Further, the signal processing circuit 105 may include a portion of detecting a foreign particle and a portion of measuring a size of the foreign particle. When the foreign object is detected by the signal processing circuit 105, for example, an input signal is binarized and a signal equal to or larger than a binarized threshold is determined as the foreign object and is outputted. Further, although according to the signal processing circuit 105, the size of the foreign object is also measured, a detailed description will be given later of the processing. Further, the stage unit 107 is provided with a mechanism of, for example, moving the object to be inspected in the horizontal and vertical directions and rotating the object to be inspected 102. Further, the autofocus illumination unit 108 converges light irradiated from, for example, a white light source of an Hg lamp or the like or a laser light source of He—Ne or the like onto the object to be inspected 102. The autofocus light detection unit 109 is used to detect light reflected from the object to be inspected 102 and irradiated from the autofocus illumination unit 108, and may include a mechanism of detecting a position of light, for example, a position sensor. Further, information provided by the autofocus light detection unit 109 is transmitted to the stage unit 107 and is used for controlling the stage. Further, although the example shown in the drawing, in which the illumination optical unit 101 is used to illuminate the object to be inspected 102 from one direction, there may be constructed an optical unit in which the object to be inspected 102 is illuminated from two or more directions. Further, although according to the example of the drawing, respective ones of the optical pick-up unit 103 and the optical detection unit 104 are provided and the object to be detected 102 is detected from one direction, there may be constructed a mechanism for detecting the object to be inspected 102 from two or more directions.

Next, an overall inspection system for inspecting a foreign particle or defect on a sample according to the present invention is described with reference to FIG. 2. That is, the system comprises a foreign particle inspection apparatus 1301 according to the present invention, a data server 1302, a review apparatus 1303, an electric test apparatus 1304, an analysis apparatus 1305 and a network 1306 connecting the respective apparatus. In this case, the review apparatus 1303 is, for example, a length measuring SEM. The electric test apparatus 1304 is a tester and the analysis apparatus 1305 is an apparatus of analyzing content of a foreign particle such as EDX. Further, the data server 1302 is a computer capable of collecting and storing inspection data of the foreign particle inspection apparatus 1301, a review result of the review apparatus 1303, further, a test result of the electric test apparatus 1304 and an analysis result of the analysis apparatus 1305 and the network 1303 is a communication network by Ethernet.

Next, an explanation will be given of operation of the system using the foreign particle or defect inspection system. After carrying out inspection by the foreign particle inspection apparatus 1301, a foreign particle which needs the countermeasure is selected by the method, explained above. The inspection result of the foreign particle inspection apparatus 1301, for example, a consecutive number in detecting the foreign particle, position information of the foreign particle or size information of the foreign particle, is added with information of the selected foreign particle and is transmitted to the data server 1302 via the network 1306. In this case, as a method of adding information of the selected foreign particle, for example, there may be added a flag of whether the countermeasure is needed or not to the inspection result. Further, in order to investigate the foreign particle detected by the foreign particle inspection apparatus 1301 in further details, the object to be inspected is moved to the review apparatus 1303. The moving operation may be carried out by manual transfer or mechanical transfer. After moving the object to be inspected to the review apparatus 1303, an access is made from the review apparatus 1303 to the data server 1302 and the review apparatus 1303 receives the inspection result from the data server 1302 via the network 1306. Further, review operation is started by using the inspection result. At this occasion, by reviewing with priority the foreign particle which needs the countermeasure by using the information added by the foreign particle inspection apparatus 1301, analysis of the foreign object constituting the cause of failure can swiftly be carried out. Further, similarly, also in the analysis apparatus 1305, by the information added by the foreign particle inspection apparatus 1301, the foreign particle which needs the countermeasure can be analyzed with priority and analysis of the cause of failure can swiftly be advanced.

These review data and the analysis result are stored in the data server 1302 and checked by a test result at the electric test apparatus 1304 to thereby enable to finally confirm whether the foreign object indicates a failure or not. When the foreign particle has not.indicated a failure, data requesting a change of a reference of a foreign particle which needs a countermeasure is transmitted from the data server 1302 to the foreign particle inspection apparatus 1301. By changing the reference of the foreign particle inspection apparatus 1301 of whether the countermeasure is needed or not, a foreign particle which needs a countermeasure can be selected with higher accuracy and the measure against the failure in semiconductor fabrication can be carried out more swiftly.

Further, although an explanation has been provided in an example of transmitting and receiving data via the network, it is not necessarily needed to transmit and receive data via the network but data may be received and delivered by a removable storage medium or printed-out paper.

Next, an explanation will be given of other way of use in the combination of the foreign particle inspection system 1301 according to the present invention and the review apparatus 1303. First, inspection is carried out by the foreign inspection apparatus 1301 and the inspection result, for example, a consecutive number in detecting a detected foreign particle, position information of the foreign particle and size information of the foreign particle is added and transmitted to the data server 1302 via the network 1306. After moving the object to be inspected to the review apparatus 1303, review operation is carried out at the review apparatus 1303 and size information of the foreign particle which is measured at the review apparatus 1303 is added to the above-described inspection result. In this case, with regard to the size information of the foreign particle, a length measuring SEM is used as the review apparatus 1303, a size in the lateral direction of the foreign particle and a size in the longitudinal direction thereof are measured by the length measuring SEM and a square root of a value produced by multiplying the size in the lateral direction by the size in the longitudinal direction may constitute the size information of the foreign particle. Next, the above-described added information is transmitted to the data server 1302, the above-described information is received by the foreign particle inspection apparatus 1301 and based on the above-described size information, the size information of the foreign particle outputted by the foreign particle inspection apparatus 1301 is corrected. As a method of the correction, for example, there is provided a method of forming a graph in which the size information from the foreign particle inspection apparatus 1301 is set to the abscissa and the size information measured by the review apparatus 1303 is set to the ordinate, plotting the size information of the same foreign particle as one point, calculating an approximated straight line by the least squares method based on the plotted data and correcting the size information of the foreign particle inspection apparatus 1301 by the approximated straight line. Further, although in this case, the data is approximated by the straight line as correcting means, the data may be corrected by a higher order curve, a logarithmic curve or an exponential curve or a combination of a plurality of curves.

Further, an explanation will be given of other way of use of the combination of the foreign particle inspection system 1301 according to the present invention and the review apparatus 1303. First, inspection is carried out by the foreign particle inspection apparatus 1301, the inspection result, for example, a consecutive number in detecting the detected foreign particle, position information of the foreign particle or size information of the foreign particle is added and transmitted to the data server 1302 via the network 1306. After moving the object to be inspected to the review apparatus 1303, when the review operation is carried out by the review apparatus 1303, in conformity with the size information of the foreign particle measured by the foreign particle inspection apparatus 1301, magnification of the review apparatus 1303 in the review operation is changed to thereby enable to carry out the review operation with excellent efficiency. That is, in the case in which the size information of the foreign particle provided by the foreign particle inspection apparatus 1301 indicates a small foreign particle, the review operation is carried out with high magnification and in the case in which the size information of the foreign particle indicates a large foreign particle, the review operation is carried out with low magnification. Further, although according to the example, an explanation has been given of the example of outputting the size information of the foreign particle from the foreign particle inspection apparatus 1301, otherwise, information of review magnification or a scope of field of review of the review apparatus 1303 may be outputted.

(Measurement of Size of Particle)

Next, an explanation will be given of a processing of measuring a size of a foreign particle by the foreign particle or defect inspection system according to the present invention with reference to FIGS. 3(*a*) and 3(*b*) and FIGS. 4(*a*), 4(*b*) and 4(*c*).

Figure 3A:
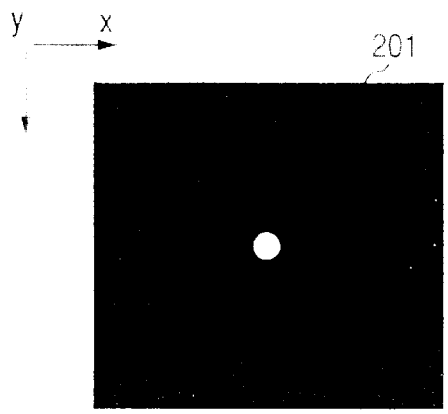
FIGS. 3(a) and 3(b) are a view showing image data when foreign particles are present and a diagram showing a distribution of a signal intensity when foreign particle data is measured.
Figure 3B:
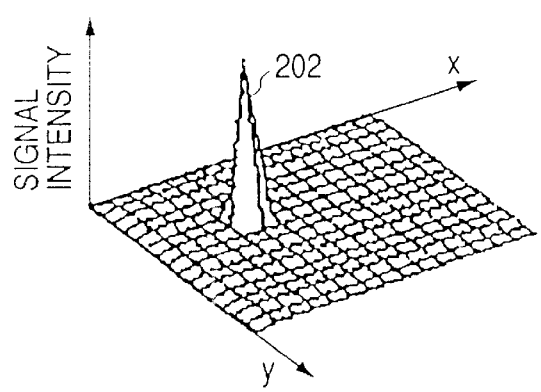

FIG. 3(*a*) shows an example of an image processed by the signal processing circuit 105 in the presence of a foreign particle and foreign particle data 201 is present at a central portion of the image. The foreign particle data 201 is outputted from the optical detection unit 104 and is processed as data having a graduation value by the signal processing circuit 105. FIG. 3(*b*) represents FIG. 3(*a*) three-dimensionally, x and y axes are coordinate axes for determining a position in the image and z axis is plotted with a signal intensity at the position and the signal intensities are connected by lines. In FIG. 3(*b*), there is shown waveform data of the foreign particle data 201 by a waveform 202. The waveform 202 becomes a waveform which can be approximated by a Gaussian distribution from properties of the illumination optical unit 101 and the optical pick-up unit 103 and a width and a height of the Gaussian distribution are changed by the size of the foreign particle of the object to be inspected. Further, the width and the height of the distribution are changed also by illuminance of laser illumination used in the illumination optical unit 101. Therefore, a shape or a characteristic amount of the distribution is measured beforehand with regard to various standard particles by apparatus according to the present invention and a result of the measurement is compared with the detected waveform 202 to thereby enable to provide size information of detected foreign particle.

At this occasion, detection of foreign particle and provision of size information of detected foreign particle may be carried out at different timings. That is, in the signal processing circuit 105, whereas a portion thereof for detecting a foreign particle detects the foreign particle in synchronism with a detection signal transmitted from the optical detection unit 104, a portion thereof for measuring the size of the foreign particle processes a signal of the foreign particle detected by the portion of detecting the foreign particle as explained above asynchronously from the detection signal transmitted from the optical detection unit 104 to thereby enable to provide the size information of the detected foreign particle. The asynchronous processing of the foreign particle detection signal may be carried out in parallel with the foreign object detection processing or may be carried out after finishing the foreign particle detection processing.

In this case, as a method of comparing a waveform of a standard particle with the waveform 202 of the foreign particle, a sum (integral) of signal intensities of portions of the foreign particle data 201, that is, volume data of waveform 202 may be measured and volume data of the standard particle and volume data of the foreign particle data 201 may be compared with each other. However, in the case in which there is a difference in the illuminance of the illumination optical unit 101 in measuring the data, the respective volume data are divided by the respectively used illuminances of the illumination optical unit 101 to thereby normalize the respective volume data or the volume data of the foreign particle data 201 or the standard particle is multiplied by a ratio of the illuminances to thereby correct the volume data.

Further, as other method of comparing the waveform, a maximum value of the signal intensity of the waveform 202 or a width of the waveform 202 may be compared.

In the following, an explanation will be given of a method of calculating the maximum value of the signal intensity in the above-described methods in reference to FIGS. 4(*a*), 4(*b*) and 4(*c*). FIGS. 4(*a*), 4(*b*) and 4(*c*) show an example of waveform data of foreign particle data similar to the waveform 202 in which FIG. 4(*a*) shows an example in which a signal waveform of foreign particle data provided by the optical detection unit 104 becomes a waveform of a mountain having a peak, showing that the signal does not reach a saturated area of the optical detection unit 104. Further, FIG. 4(*b*) shows an example in which a signal waveform of foreign particle data constitutes a waveform of a trapezoid at the top, showing that the signal reaches the saturated area of the optical detection unit 104 and there is present no data above the saturated area.

Figures 4A, 4B, 4C:
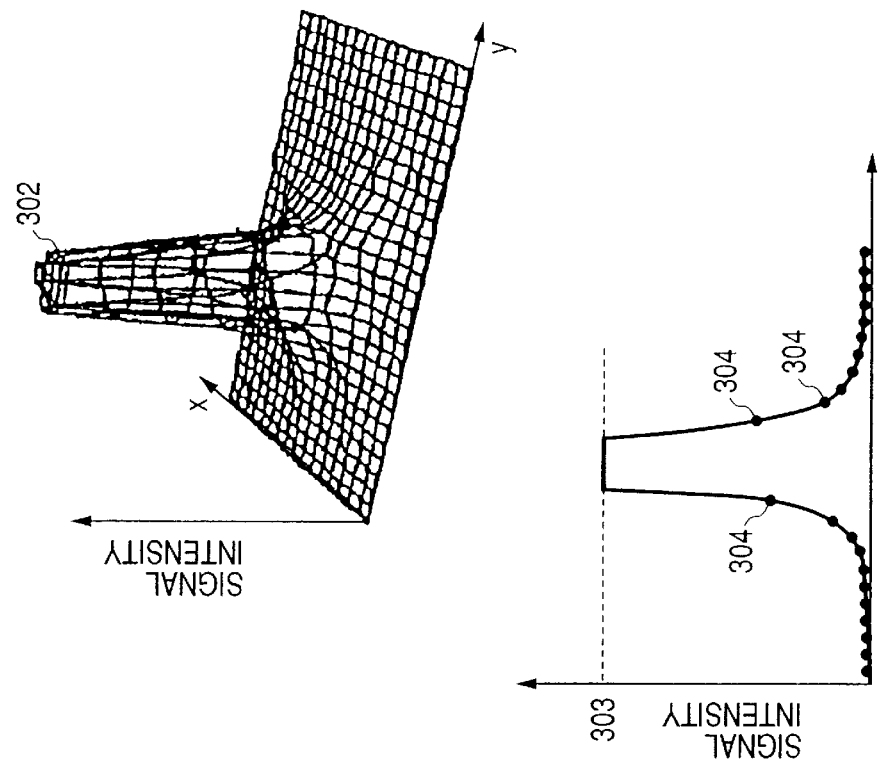
FIGS. 4(a), 4(b) and 4(c) are diagrams comparing distributions of signal intensities of two kinds and an explanatory diagram for calculating a maximum value of the signal intensity.

A maximum value of the signal intensity is constituted of a value maximized in comparison with signal intensities of respective pixels of the waveform when a signal waveform as shown by FIG. 4(*a*) is illustrated, that is, the maximum value of the signal intensity is constituted of a peak point signal intensity 301. Further, when a signal waveform as shown by FIG. 4(*b*) is illustrated, the maximum value of the signal intensity is calculated by carrying out a calculation shown below.

First, in a saturated area 302, a maximum value of a saturated area is calculated with regard to x and y directions.

FIG. 4(*c*) shows a section of FIG. 4(*b*) according to the maximum length portion. In FIG. 4(*c*), the abscissa is a coordinate axis showing positions of pixels at the maximum length portion and the ordinate is a coordinate axis showing signal intensity. Further, a signal intensity 303 indicates a saturation level of the optical detection unit 104. With regard to the section, three or more points of unsaturated signals 304 are selected. In this case, an explanation will be given such that three points are selected. As selected points, three points are selected for unsaturated signals of the section portion from signals having larger signal intensities. When respective coordinates of data of the selected three points are designated by x1, x2 and x3 and signal intensities of the respectives are designated by z1, z2 and z3, by using unknown quantities of k, σ and u, Equations of Gaussian distribution are provided as follows.

$$z1 = k/\sigma \times \exp(-(x1-u)2/(2 \times \sigma 2))$$

$$z2 = k/\sigma \times \exp(-(x2-u)2/(2 \times \sigma 2))$$

$$z3 = k/\sigma \times \exp(-(x3-u)2/(2 \times \sigma 2))$$

The unknown quantities of k, σ and u can be calculated by simultaneously establishing the above three equations. Further, when calculated values of k and σ are used, the maximum value of the signal intensity of FIG. 3(*b*) can be calculated as k/σ.

Further, although in this case, there is shown an example of calculation by using the unknown quantity of u, the unknown quantity of u may not necessarily be used. In that case, two points of the signals 304 are selected. As selected points, there are selected two points of unsaturated signals of the section portion from larger ones of signal intensities. When with regard to data of the two points, respective coordinates are designated by x1 and x2 and respective signal intensities are designated by z1 and z2, by using unknown quantities of k and σ, Equations of Gaussian distribution are provided as follows.

$$z1 = k/\sigma \times \exp(-(x1)2/(2 \times \sigma 2))$$

$$z2 = k/\sigma \times \exp(-(x2)2/(2 \times \sigma 2))$$

The unknown quantities of k and σ are calculated by simultaneously establishing the above two equations and accordingly, when the values of k and σ are used, the maximum value of the signal intensity of FIG. 3(*b*) can be calculated as k/σ.

By comparing the maximum value of the signal intensity provided by the above calculation between a value of the standard particle and the value of the detected foreign particle, the size of the foreign particle can be measured.

Further, although an example of using laser in the illumination optical unit 101 is described according to an embodiment of the present invention, measurement using white light may be used. Further, with regard to a foreign particle on a circuit pattern having repeatability, the above-described size measuring processing may be carried out after calculating a difference between an image where the foreign particle is present and an image where the foreign particle is not present on the repeated pattern. Further, regardless of presence or absence of the repeatability, with regard to a foreign particle on a circuit pattern or on a film, for example, an oxide film or a metal film, in the case in which scattered light data is provided from the circuit pattern or film beforehand, data of size of the foreign particle may be corrected by using the data. Further, although an explanation has been given here that in order to measure the size of the foreign particle, the size of the foreign particle is compared with the size of the standard particle, the size of the foreign particle may be compared with that of a foreign particle the size of which has already been known.

Figure 15:
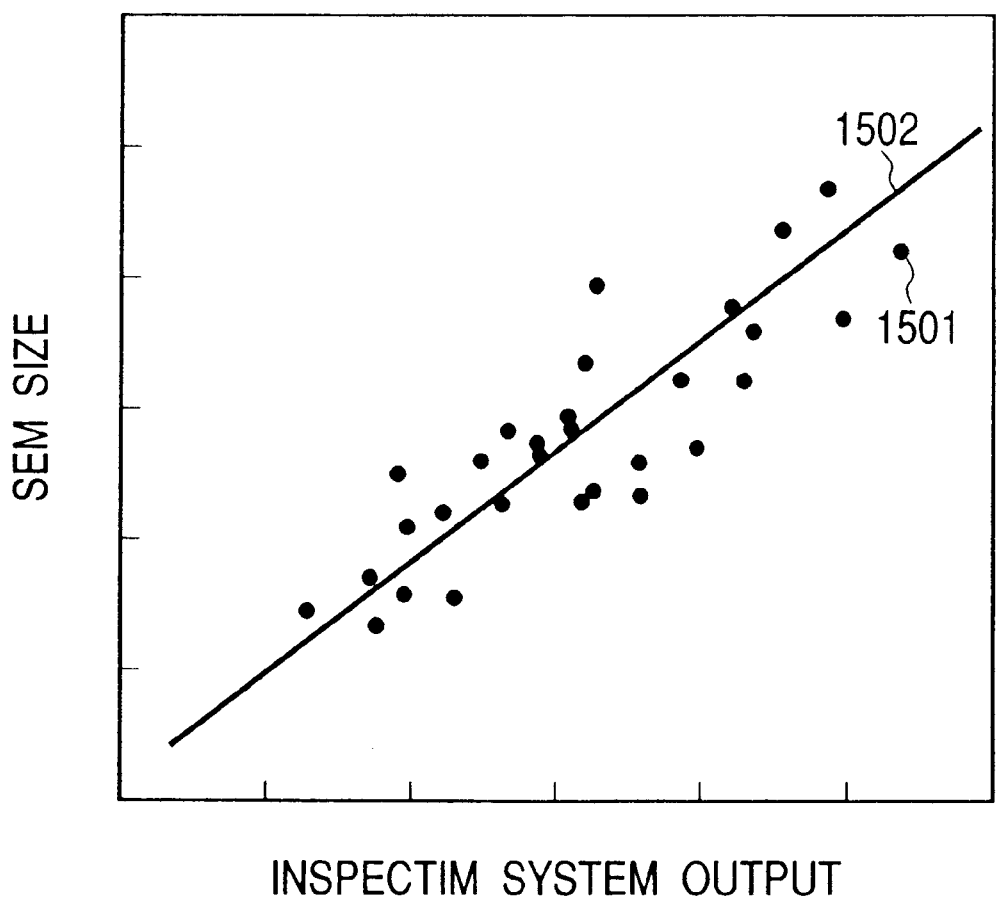
FIG. 15 is a diagram for explaining an output of an inspection system and a method of correcting a size of a foreign particle.

Here, an explanation will be given of an example of a method of correcting data using a foreign particle the size of which has already been known in reference to FIG. 15. FIG. 15 is a graph the abscissa of which is set with an output value from the foreign particle inspection system according to the present invention and the ordinate of which is set with the size of the foreign particle. Further, plot point 1501 indicates data with regard to one foreign particle and FIG. 15 shows a state in which data of a plurality of foreign particles are displayed. Further, an approximated curve 1502 is an approximated curve calculated by the least squares method based on data of the plot points 1501. Here, when the abscissa of the graph is designated by notation x and the ordinate is designated by notation y, the above calculated approximated curve equation can be represented as y=f (x). As the correction method, the above approximated curve equation may be used and the size of the foreign particle after correction may be constituted of a value of y calculated by substituting an output from the foreign particle inspection system for x of the approximated curve equation.

Here, with regard to the size of the foreign particle, for example, the size in the lateral direction and the size in the longitudinal direction of the foreign particle may be measured by the length measuring SEM and a square root of a value produced by multiplying the size in the lateral direction by the size in the longitudinal direction may constitute the size of the foreign object, further, other than the example, the major axis of the foreign particle may be used or the minor axis of the foreign particle may be used. Further, although according to the example, the square root is calculated, a larger value of the size in the longitudinal direction and the size in the lateral direction may constitute the size of the foreign particle or an average value of the size in the longitudinal direction and the size in the lateral direction may constitute the size of the foreign particle. Further, the approximated curve may be approximated by a first order curve, that is, a straight line or a higher order curve, a logarithmic curve or an exponential curve or a combination of a plurality of curves.

Further, when the approximated curve is changed in accordance with the shape of the foreign particle, in the case in which a correlation is excellent between the size of the foreign particle calculated as described above and the size of the foreign particle measured by the length measuring SEM is excellent, the approximated curve may be changed in accordance with the shape of the foreign particle. In this case, when a ratio of a size of the foreign particle measured from above to a size thereof measured from the side differs, the difference in the shape of the foreign particle is, for example, a difference between sphere and flat plate or a difference between the foreign particle and scratch. Further, although an explanation has been given of an example of the difference in the shape of the foreign particle in the above-described, the approximated curve may be changed in accordance with the difference in a position of detecting the foreign particle relative to an uninspected object, for example, by whether the foreign particle is a foreign particle on the circuit pattern or a foreign particle of a portion having no pattern. Further, the approximated curve may be changed in accordance with a surface state of an uninspected object, for example, whether the surface is made of an aluminum film or a tungsten film.

In the above-described explanation, inspection of foreign pattern is carried out by scattered light. The merit of this method resides in that discovery of foreign pattern can be carried out efficiently. Further, when the size of the foreign pattern is calculated by the above-described method, there is achieved the merit in which a special light source is not needed for measuring the size and discovery of the foreign particle and measurement of the size can be carried out by the same light source by scattered light.

(Analysis of Cause of Failure and Display of Result)

Next, an explanation will be given of a procedure of analyzing cause of failure and a procedure of displaying a result to a user when a size of a foreign particle is measured by the foreign particle or defect inspection system according to the present invention in reference to FIG. 5(*a*) through FIG. 10.

As one of important idea of the present invention, there is a case in which size information of a foreign particle is used for analyzing cause of failure. An explanation will be given as follows of effectiveness in using the size information of the foreign particle for analyzing the cause of failure.

Figure 5A:
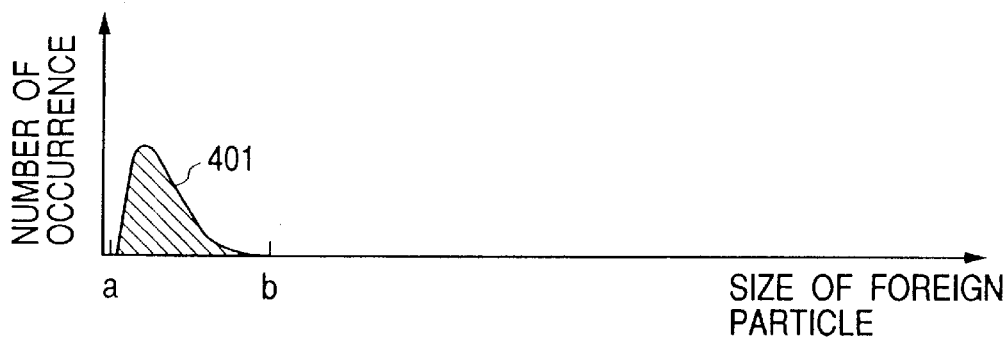
FIGS. 5(a), 5(b) and 5(c) are diagrams showing that a relationship between a size of a foreign particle and the number of occurrence differs by cause of failure.
Figure 5B:
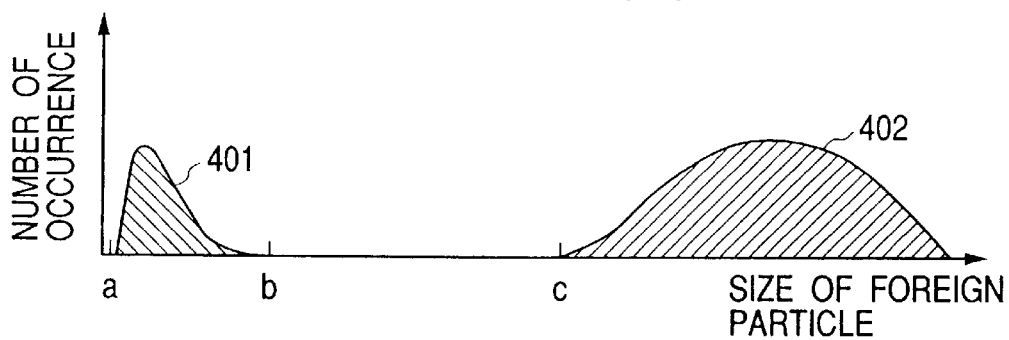

In this case, assume that a foreign particle is detected from a wafer subjected to a semiconductor fabrication apparatus, for example, an etching apparatus and a relationship between a size of the foreign particle and the number of occurrence is as shown by FIGS. 5(*a*), 5(*b*) and 5(*c*). An area 401 in FIG. 5(*a*) shows a distribution of foreign particles which constantly occur in the process of the etching apparatus. In this case, sizes of foreign particles concentrate at portion a through b and one gradual mountain is produced in accordance with the sizes of the foreign particles.

In contrast thereto, FIG. 5(*b*) shows an example of a distribution of occurrence of foreign particles when the system is abnormal and in this case, in addition to the foreign particles under the stationary state indicated by the area 401, many of large foreign particles (portion having size of c or more) as indicated by an area 402 occur. As cause therefor, it is conceivable that an accumulated matter accumulated on an inner wall face of the etching apparatus during the etching processing is peeled off and dropped from the wall face. Further, FIG. 5(*c*) also shows an example of a distribution of occurrence of foreign particles in abnormal time. In this case, it is shown that in addition to the foreign particles under the stationary state, the sizes of the foreign particles concentrate on a portion of d through e. As a cause therefor, it is conceivable that a specific pattern is peeled off and flown during the etching processing.

In this way, according to a fabrication system of a semiconductor or the like, there is a correlation between a size of a generated foreign particle and cause of occurrence of the foreign particle and by controlling a situation of occurrence of foreign particle having a specific size, the cause of occurrence of the foreign particle in the fabrication system can swiftly be known. That is, by investigating a relationship between a size of a foreign particle and the number of occurrence, a cause of failure can be clarified.

Further, naturally, the above-described values of a through e or the like are values changed by the fabrication apparatus, fabrication process or the like, further, according to a foreign particle which occurs by other cause, there is a case in which a distribution of a different size is shown and accordingly, there may be used data in conformity with a distribution of a size of a foreign particle in accordance with cause of occurrence. Further, although according to the example, cause of occurrence of foreign particle is intended to specify by two ranges, the distribution may be divided in two or more areas.

Next, a specific explanation will be given of a function of analyzing cause of failure.

Figure 6:
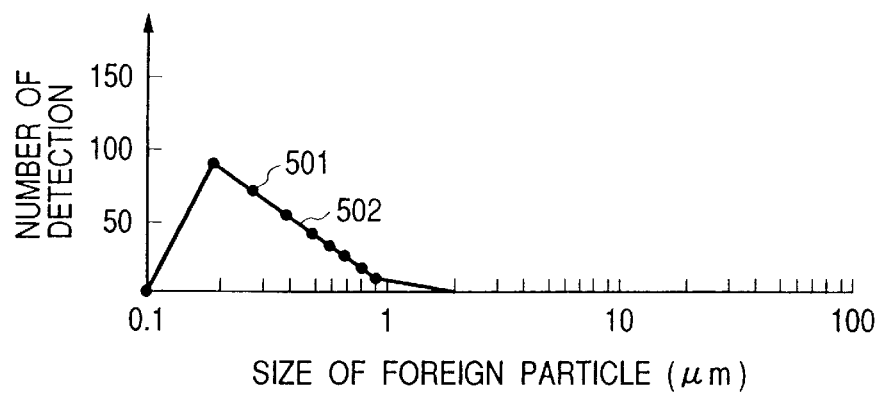
FIG. 6 is a diagram showing the number of detection of foreign particles and sizes of foreign particles by a polygonal graph.

First, an explanation will be given of display of sizes of foreign particles and the number of detection by the data display unit 106. The data display unit 106 displays a graph of a distribution of sizes of foreign particles as described above, that is, a graph by which a relationship between sizes of foreign particles and the number of detection of the foreign particles is known. FIG. 6 is a graph in which sizes of foreign particles as shown by the abscissa and the number of detected foreign particles as shown by the ordinate are arranged. Point 501 indicates the number of detection in accordance with the size and according to the example of the graph, there is shown data of 0.1 $\mu$m unit. Further, graph 502 is a line connecting the points 501 by straight lines. By displaying the graph as in the example, a way of a distribution of foreign particles detected from the object to be detected 102 can swiftly be found.

In this case, a minimum value of the abscissa may be a minimum detection size of the foreign particle inspection apparatus or a size of a foreign particle which is intended to control by a semiconductor fabrication line. Further, graduation may be displayed in logarithm as in the graph or may be displayed linearly and the unit of graduation may be made variable. Further, display ranges of the respective axes may be fixed or may be variable, for example, foreign particles of a specific cause of occurrence may be displayed by displaying only a specific size. Further, the contents shown by the ordinate and the abscissa may be switched and a density of foreign particles may be represented in place of the number of detected foreign particles. Further, although according to the example, a graph is displayed, other than the graph, an average value of graph, a standard deviation value or a dispersion value of graph may be displayed. Further, although according to the example, foreign particle data of one sheet of wafer is displayed as graph of one sheet, one sheet of the wafer may not necessarily be displayed but an average value or a standard deviation value or a dispersion value of foreign particle data of a plurality of sheets of wafers may be displayed, further, foreign particle data of a plurality of sheets of wafers may be displayed respectively in parallel.

Figure 7:
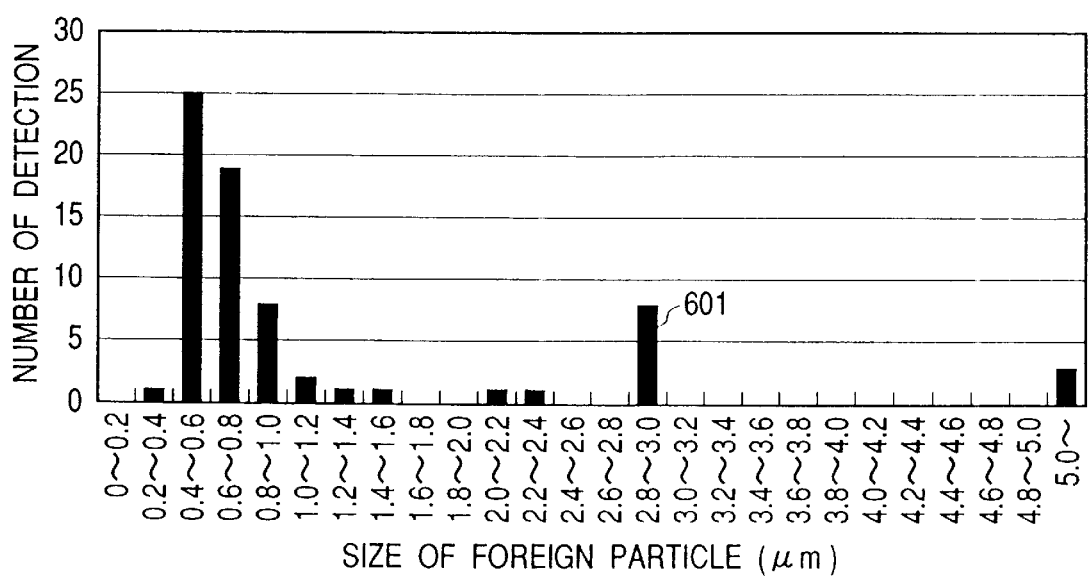
FIG. 7 is a diagram showing the number of detection of foreign particles and sizes of foreign particles by a histogram.

Further, display of graph may be carried out by a histogram as shown by FIG. 7. The graph of FIG. 7 is a graph in which sizes of foreign particles are shown by the abscissa and the number of detected foreign particles is shown by the ordinate similar to FIG. 6. According to the graph, sizes of foreign particles are displayed by being divided in respective sections in the abscissa and FIG. 7 shows a case in which the data sections are constituted of a unit of 0.2 $\mu$m. Further, there may be added a function in which when a bar graph is selected, position information of detected foreign particles of a selected portion is displayed.

Figure 8A:
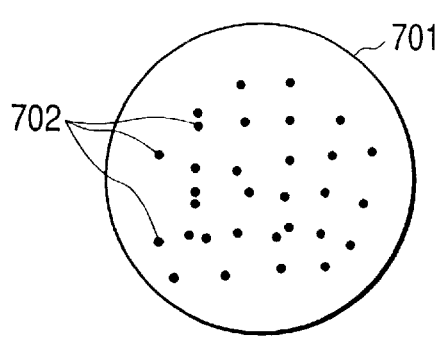
FIGS. 8(a) and 8(b) are schematic views specifically showing foreign objects having a specific size on a wafer.
Figure 8B:
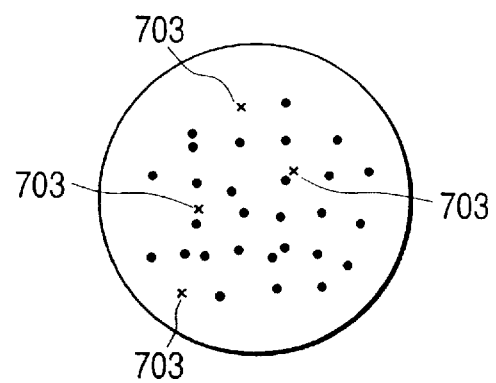

An explanation will be given of a function of displaying position information of detected foreign particles. FIG. 8(a) displays position information of all of detected foreign particles detected by foreign particle inspection. In the drawing, there is shown, for example, presence of detected foreign particles 702 on an outer configuration 701 of a semiconductor wafer of 8 inch. In this case, there is provided a function of changing display of a section of a bar graph 601, that is, foreign particles 703 of 2.8 $\mu$m through 3.0 $\mu$m as shown by FIG. 8(b) when the bar graph 601 in FIG. 7 is clicked or double-clicked. Thereby, positions of foreign particles having specific sizes on the object to be inspected 102, can swiftly be grasped.

Next, an explanation will be given of a control method when the statistics is taken time-sequentially with regard to sizes of specific foreign particles in reference to FIGS. 9(a), 9(b) and 9(c).

Figure 9A:
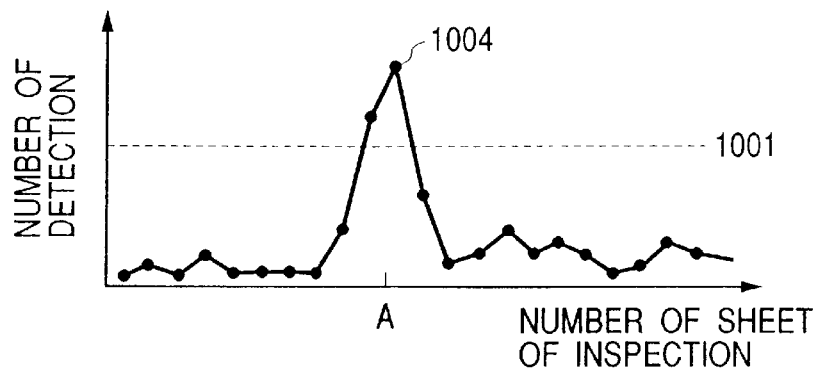
FIGS. 9(a), 9(b) and 9(c) are graphs showing a transitional change of the number of detection for respective sizes of specific foreign particles.
Figure 9B:
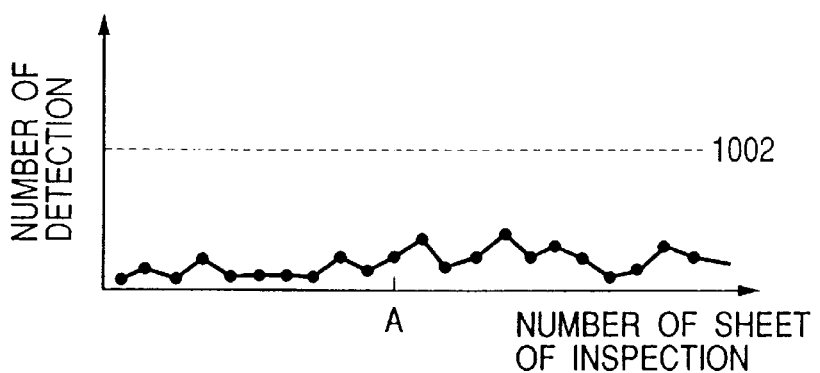
Figure 9C:
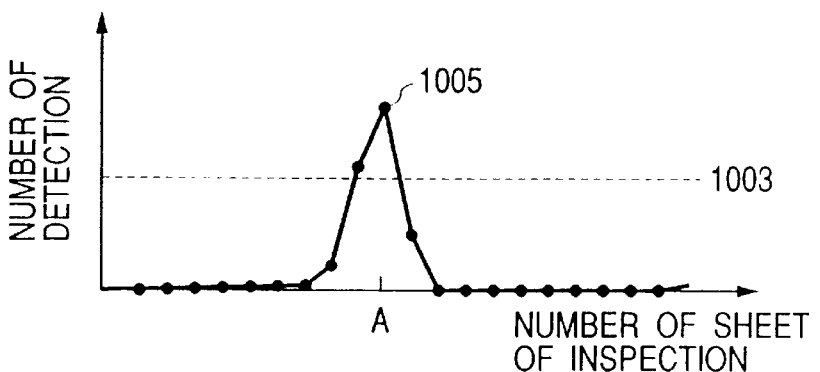

Here, FIG. 9(a) displays a time-sequential transitional change of a sum of all of foreign particles detected by the foreign particle detection system regardless of their sizes, FIG. 9(c) displays a time-sequential transitional change of a sum of foreign particles having sizes of 2.8 through 3.0 ($\mu$m) of foreign particles shown in the example of FIG. 7 and FIG. 9(b) displays a time-sequential transitional change of a sum of foreign particles having sizes other than specified above.

Further, thresholds 1001, 1002 and 1003 show control reference values of the number of foreign particles, showing that when foreign particles more than the thresholds are detected, the wafer is diagnosed to be abnormal. That is, it is determined that in FIG. 9(a), a peak value 1004 around inspection time point A indicates abnormality.

However, by only the statistics of FIG. 9(a), although some abnormality is predicted to occur, it is difficult to clarify the cause.

In the meantime, when sizes of foreign particles are controlled in accordance with the sizes by the inspection method of the present invention, a significant peak 1005 is observed at time point A of FIG. 9(c) and it is known that foreign particles having sizes of 2.8 through 3.0 ($\mu$m) particularly concentrate on a lot inspected at the time point. Therefore, there is not a portion exceeding the threshold in FIG. 10(b), the peak value 1005 is detected in FIG. 10(c) and it can be predicted from the reason shown in FIG. 5(c), that peeling off and flying a pattern having the size on the wafer in the etching processing, is the factor of particularly many foreign particles and an effective failure countermeasure such as checking the etching apparatus can swiftly be carried out.

Next, an explanation will be given of an example of displaying the failure cause to a user in reference to FIG. 10.

The foreign particle or defect inspection system according to the present invention is provided with a function of analyzing sizes of foreign particles and the number of detection of foreign particles and displaying the failure cause to the user.

Figure 5C:
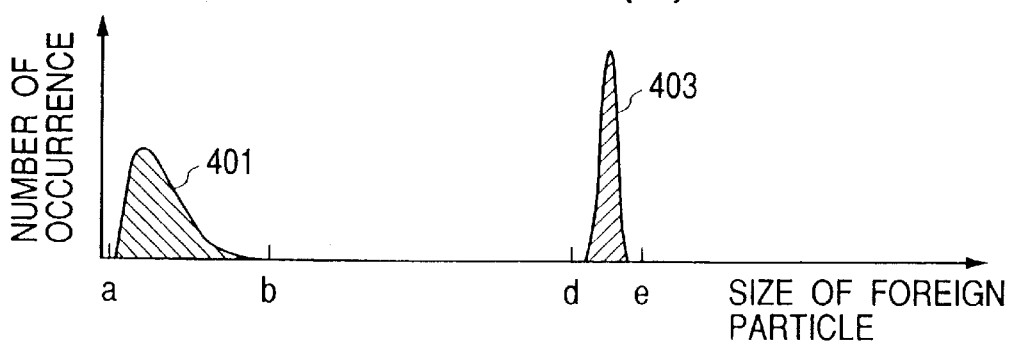

For example, assume that the cause pointed out in reference to FIG. 5(c) is taken as a model and a result of the graph shown by FIG. 7 is provided as a result of inspection. Further, assume that a section of d through e corresponds to 2.8 $\mu$m through 3.0 $\mu$m of FIG. 7. Therefore, when the inspection result shown by FIG. 7 is provided, a screen shown by FIG. 10 is displayed and a result of analyzing the failure cause is clearly shown to the user.

(Inspection of Foreign Particles in Accordance With Areas and Analysis of Failure Cause)

Next, an explanation will be given of an example of controlling foreign particle data in accordance with areas on a wafer and carrying out failure countermeasure by the foreign particle or defect inspection system according to the present invention in reference to FIG. 11 through FIG. 14.

Figure 11:
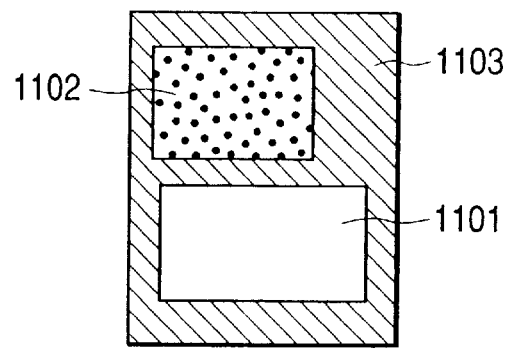
FIG. 11 is a view schematically showing areas of a semiconductor wafer.

FIG. 11 is a view schematically showing areas of a semiconductor wafer.

Figure 12A:
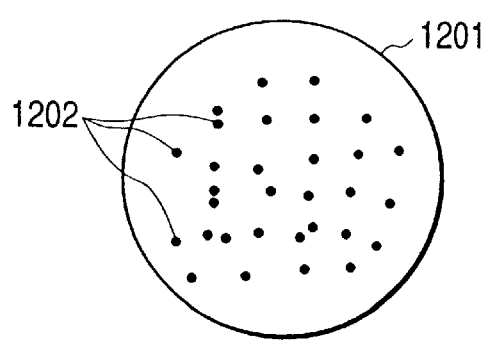
FIGS. 12(a) and 12(b) are schematic views specifically showing foreign particles having a specific size on a wafer when foreign particle data is controlled for respective areas.
Figure 12B:
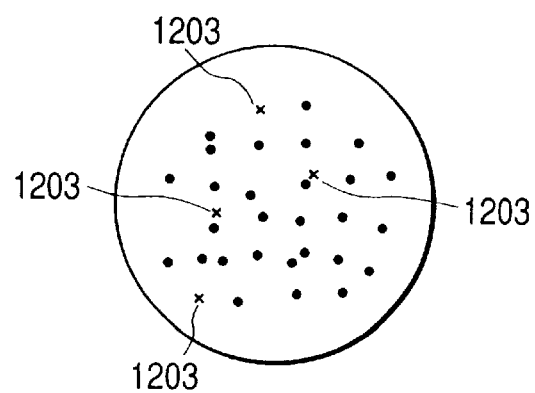

FIGS. 12(a) and 12(b) are schematic views specifically showing foreign particles having specific sizes on the wafer when foreign particle data is controlled in accordance with the areas.

Figure 13:
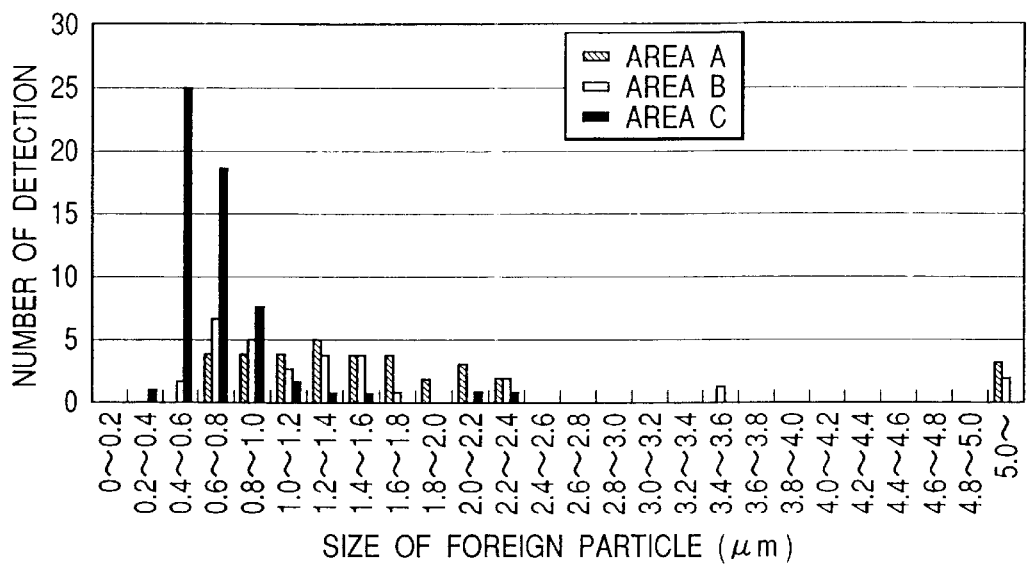
FIG. 13 is a diagram showing a graph displaying the number of detection for respective sizes of foreign particles for respective areas (part 1)
Figure 14:
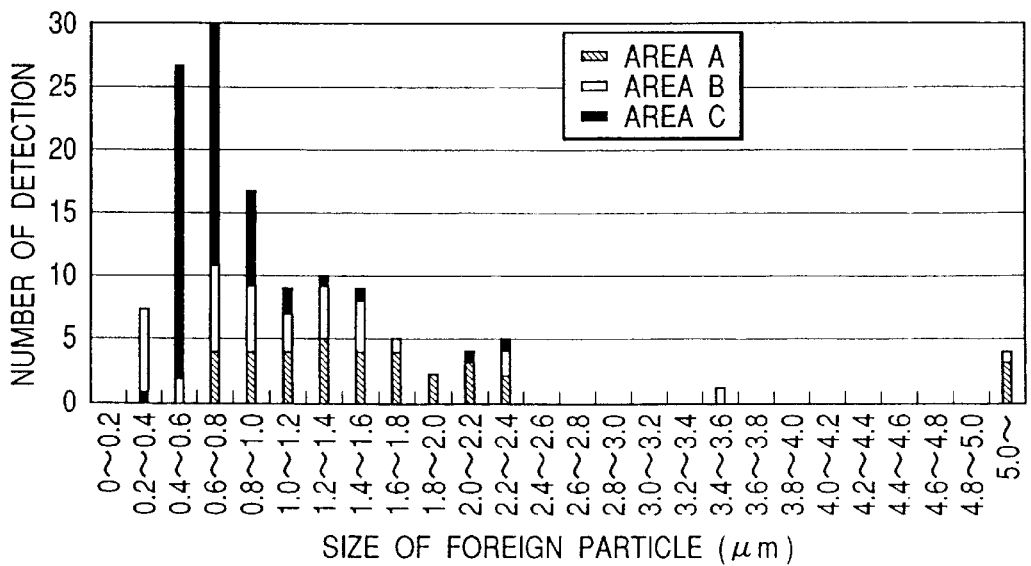
FIG. 14 is a diagram showing a graph displaying the number of detection for respective sizes of foreign particles for respective areas (part 2)

FIG. 13 and FIG. 14 are drawings showing graphs displaying the number of the detection in accordance with sizes of foreign particles by the areas.

Generally, when a pattern of a chip is formed on a semiconductor wafer, the pattern is not necessarily formed uniformly but there is a portion where a density of forming the pattern is high and there is portion where the density is low. For example, when a chip shown by FIG. 11 is of a microprocessor, for example, the pattern is divided into an area 1101 of a memory cell circuit portion, an area 1102 of an input and output circuit portion of data and an area 1103 of a portion where a circuit pattern is not present. Normally, an integration degree of circuit pattern differs by the areas 1101, 1102 and 1103. Therefore, as the result, sizes of foreign particles constituting the failure cause also differs by the respective areas. That is, sizes of foreign particles to be controlled and analyzed differ in accordance with the areas in the chip. Specifically speaking, for example, in the case in which a foreign particle having a size equal to or larger than a constitutes a failure in the area 1101, a foreign particle having a size equal to or larger than $\beta$ constitutes a failure in the area 1102 and a foreign particle having a size equal to or larger than $\gamma$ constitutes a failure in the area 1103, the area information and the size information of foreign particles constituting failure are previously provided to the inspection system as control data. With regard to a method of inputting the area information and the size information of foreign particles constituting failure, the information may directly be inputted by providing a screen of inputting coordinate values and sizes of foreign particles in the inspection system or the areas may be selected from an image produced by inputting an optical image of the wafer by a TV camera or the like. Further, data may be downloaded from a higher system or data may be read from a removable storage medium, for example, a floppy disk to the inspection system.

As described above, inspection of the object to be inspected is carried out by providing information of areas and sizes of foreign particles determined to be failure to the inspection system. Further, the areas are determined by the position information of detected foreign particles at the inspection system and it is determined whether the failure cause is constituted by comparing the size information of detected foreign particles with size information of foreign particles constituting the failure.

As a result, by clearly showing foreign particles constituting the failure cause to the user by changing output display modes of foreign particles determined to constitute the failure cause and foreign particles determined not to constitute the failure cause, the user can immediately find the foreign particles constituting the failure cause.

The method is specifically shown as follows in reference to FIGS. 12(*a*) and 12(*b*).

Positions of detected foreign particles 1202 are shown and outputted in a wafer 1201 shown by FIG. 12(*a*). Conventionally, there is provided a result of detection as shown by FIG. 12(*a*) and therefore, in analyzing a failure cause, foreign particles are pertinently selected and the foreign particles are analyzed. Therefore, a probability of capable of selecting foreign particles to be analyzed truly is low and a time period is required in analyzing the failure cause. However, by using the previous determination, as shown in FIG. 12(*b*), by changing display of foreign particles determined to constitute the failure cause, that is, foreign particles 1203 to be analyzed, foreign particles 1203 to be analyzed are easily selected from the detected foreign particles, the probability of capable of selecting foreign particles to be analyzed is increased and analysis of the failure cause can swiftly be carried out. Further, although in FIG. 11, as a method of changing display, the display is shown by changing the display pattern, otherwise, color or size of the display pattern may be changed. Further, only foreign particles constituting the failure cause may be displayed. Further, although according to the embodiment, as area classification, area classification in the chip is carried out, sizes of foreign particles to be controlled may be changed by carrying out area classification in a wafer face, for example, by carrying out area classification in accordance with a distance from a wafer center to a wafer edge. Further, layout of the semiconductor chip may be displayed in the configuration 1201 of the wafer.

Next, an explanation will be given of a method of grasping the number of detecting foreign particles and carrying out failure countermeasure in accordance with areas in reference to FIG. 13 and FIG. 14.

In this example, assume that one wafer is categorized into three areas. Assume that the areas are area A, area B and area C and the number of foreign particles are detected in accordance with areas. Further, the result is displayed to the user as graphs in accordance with areas.

For example, as shown by FIG. 13, a size of a foreign particle is indicated by the abscissa, the number of detection of foreign particles is designated by the ordinate, the area A, the area B and the area C are classified by colors and the size of the foreign particle is displayed by a graph to horizontally align for respective categories.

Further, as shown by FIG. 14, the size of the foreign particle may be displayed by a graph to vertically align for the receptive categories.

Specifically, for example, in the case of a semiconductor wafer, three areas are a memory cell circuit portion, a circuit portion other than the memory cell circuit and a portion having no circuit pattern. By displaying foreign particles as shown by FIG. 13 or FIG. 14, control of foreign particles in accordance with areas is facilitated. In this case, according to a method of inputting area information, the area information may directly be inputted by providing a screen for inputting coordinate values or sizes of foreign particles to the inspection system or the areas may be selected from an image produced by inputting an optical image of a wafer by a TV camera or the like. Further, data may be downloaded from a higher system or data may be read from a removable storage medium, for example, a floppy disk to the inspection system.

Now, an explanation will be given of a method of counting the number of detection for respective sizes of foreign particles in accordance with areas to thereby find a failure product.

As described above, when the foreign particles are present for the respective areas, sizes of the foreign particles determined to be failure differ. At a certain area, the area is constituted of a circuit which is not so fine and therefore, even when a comparatively large foreign particle is adhered thereto, the foreign particle may not be regarded as a failure and at other area, the area is constituted of a fine circuit and there is also a case in which a trouble is caused even with a comparatively small foreign particle. Thresholds of alarming for the respective areas are set to $\alpha$, $\beta$ and $\gamma$ for area A, area B and area C$\alpha$, $\beta$ and $\gamma$ are set as follows, for example, by the example shown by FIG. 13 and FIG. 14.

$\alpha$=1.0 ($\mu$m)

$\beta$=1.6 ($\mu$m)

$\gamma$=2.0 ($\mu$m)

According thereto, the total number of particles detected by foreign particles having sizes exceeding thresholds for respective areas, are as follows.

Area A 24 particles

Area B 3 particles

Area C 1 particle

Therefore, apparently, foreign particles detected in area C are very many, however, these do not effect influence on the quality of the product so much, in contrast thereto, in area A, although the number of foreign particles is not as large as that in area C, there is a high possibility of influencing on the quality of the product thereby and accordingly, there is a high probability that the product is determined to be a failure owing to the foreign particles adhered to area A. In this way, by providing thresholds of regarding a foreign particle as a failure in accordance with areas, the total number of detection of foreign particles exceeding the thresholds are calculated, acceptability or failure of the object to be inspected is determined and displayed to the user to thereby enable to carry out rational inspection in accordance with characteristics of the areas.

(With Regard to Optical System of Foreign Particle or Defect Inspection System)

As mentioned above, according to the description of the present invention, with regard to the optical system of the foreign particle or defect inspection system, an explanation has been given of the constitution in which by using scattered light, foreign particles are detected and sizes thereof are measured, however, the method of the present invention is applicable also to a constitution in which an optical system detects a foreign particle by reflected light and measures a size thereof. Generally, the constitution of using the scattered light is provided with excellent efficiency of inspection, however, there is a drawback in measurement accuracy and conversely, the constitution of using reflected light is provided with poor efficiency of inspection, however, the measurement accuracy is excellent. The method of the present invention is applicable to either of them.

According to the present invention, in carrying out inspection of a fabrication procedure of a semiconductor wafer and a substrate for forming a thin film and failure analysis, there can be provided the foreign particle or defect inspecting method and a system thereof capable of swiftly carrying out failure countermeasure by carrying out inspection in accordance with characteristics of a foreign particle or a pattern or characteristics of areas of an object to be inspected and failure analysis.

What is claimed is:

1. A system of inspecting a foreign particle or a defect, comprising:

illuminating means for irradiating light onto an object to be inspected;

light detecting means for detecting reflected light or scattered light from the object to be inspected by the light irradiated by the illuminating means;

defect detecting means for detecting the foreign particle or the defect by processing a detection signal detected by the light detecting means;

size information acquiring means for acquiring information of a size of the foreign particle or the defect by processing a signal of the foreign particle or the defect detected by the defect detecting means; and outputting means for outputting information of a time-sequential transitional change in numbers of each of the size of the foreign particle or defect for a visual display on a display screen, by receiving respective outputs from the defect detecting means and the size information acquiring means.

2. A system according to claim 1, wherein the outputting means outputs the information by discriminating a time-sequential transitional change in numbers of the foreign particle or defect having a specific size from other foreign particles or defects of different sizes.

3. A system according to claim 1, wherein the outputting means outputs the information by displaying the time-sequential transitional change in numbers of the foreign particle or defect on the display screen as a graph.

4. A system of inspecting a defect on a sample, comprising:

illuminating means for illuminating light onto the sample;

converging means for converging reflected light from the sample illuminated by the illuminating means;

detecting means for detecting the reflected light converged by the converging means;

signal processing means for detecting the defect on the sample by processing a detection signal from the detecting means and providing information with regard to a size of the defect; and outputting means for outputting the information of the distribution of the size of the defect provided by the signal processing means in each of a predetermined area on the sample for a visual display on a display screen.

5. A system according to claim 4, wherein the outputting means outputs the information displayed on the display screen so that a foreign particle or defect having a specific size can be identified from other foreign particles or defects having different sizes.

6. A system according to claim 4, wherein the outputting means outputs the information by graphically displaying on the display screen.

7. A method of detecting a foreign particle or a defect, comprising the steps of:

irradiating light onto an object to be inspected;

detecting reflected light or scattered light from the object to be inspected irradiated with the light;

detecting the foreign particle or the defect on the object;

providing information related to a size of the foreign particle or the defect based on the detected foreign particle or defect; and outputting information of a time-sequential transitional change in numbers of each of the provided size of the detected foreign particle or defect for a visual display on a display screen.

8. A method according to the claim 7, wherein, in the information indicating the time-sequential transitional change in numbers of the foreign particle or defect outputted, information of a specific size foreign particle or defect can be identified from information of other foreign particles or defects having different sizes.

9. A method according to the claim 7, wherein the information is outputted by graphically displaying on the display screen.

10. A method of inspecting a defect on a sample, comprising the steps of:

irradiating light onto the sample;

detecting reflected light from the sample irradiated with the light;

detecting a position of the defect on the sample;

classifying the detected defect in accordance with a size thereof asynchronously from detecting the reflected light; and outputting information of the distribution of the size of the detected defect in each of a predetermined area on the sample in accordance with the classified information of the detected defect for a visual display on a display screen.

11. A method according to the claim 10 wherein the information of a foreign particle or defect having a specific size can be identified from information of other foreign particles or defects having different sizes.

12. A method according to the claim 10 wherein the information is outputted by graphically displaying on the display screen.

13. A system of inspecting a sample for a foreign particle or defect, comprising:

illuminating means for irradiating light onto a sample to be inspected;

light detecting means for detecting reflected light or scattered light from the sample to be inspected by the light irradiated by the illuminating means;

defect detecting means for detecting the foreign particle or defect on the sample by processing a detection signal detected by the light detecting means;

size information acquiring means for acquiring information of a size of the foreign particle or defect on the sample by processing a signal of the foreign particle or defect detected by the defect detecting means; and outputting means for outputting information, on a display screen, a distribution of the size of the foreign particle or defect with information indicating a cause of the distribution of the foreign particle or defect.

14. A system according to the claim 13, wherein the information indicating a time-sequential transitional change in numbers of each of the size of the foreign particle or defect is displayed on the display screen as a graph.

15. A system according to the claim 13, wherein one or more foreign particles or defects are classified in different areas on the sample, and the information indicating the numbers of foreign particles or defects classified for different areas on the sample is displayed on the display screen as a graph.

16. A method of inspecting a sample for a defect, comprising:

irradiating light onto a sample to be inspected;

detecting reflected light or scattered light from the sample to be inspected irradiated with the light;

detecting the defect on the sample;

providing information related to a size of a detected defect on the sample; and outputting information, on a display screen, a distribution of the size of the detected defect on the sample with information indicating a cause of the distribution of the detected defect.

17. A method according to the claim 16, wherein the information indicating a time-sequential transitional change in numbers of each of the size of the defect is displayed on the display screen as a graph.

18. A method according to the claim 16, wherein one or more defects are classified in different areas on the sample, and the information indicating the numbers of defects classified for different areas on the sample is displayed on the display screen as a graph.

19. A method of inspecting a sample for a defect, comprising:

irradiating light to a sample to be inspected;

detecting reflected light or scattered light from the sample to be inspected irradiated with the light;

detecting the defect on the sample;

providing information related to a size of a detected defect; and outputting information, on a display screen, a distribution of the size of the detected defect by discriminating a specific size defect from other defects having different sizes, wherein said specific size of the detected defect is elected from statistical data of the sizes of the defects displayed on the display screen.

20. A method according to the claim 19, wherein the information indicating a time-sequential transitional change in numbers of each of the size of the defect is displayed on the display screen as a graph.

* * * * *